US 6,617,167 B2

United States Patent
Otvos et al.

(10) Patent No.: US 6,617,167 B2
(45) Date of Patent: Sep. 9, 2003

(54) METHOD OF DETERMINING PRESENCE AND CONCENTRATION OF LIPOPROTEIN X IN BLOOD PLASMA AND SERUM

(75) Inventors: James D. Otvos, Apex, NC (US); Elias J. Jeyarajah, Raleigh, NC (US); Irina Y. Shalaurova, Cary, NC (US)

(73) Assignee: LipoScience, Inc., Raleigh, NC (US)

(*) Notice: Subject to any disclaimer, the term of this patent is extended or adjusted under 35 U.S.C. 154(b) by 0 days.

(21) Appl. No.: 10/208,371

(22) Filed: Jul. 30, 2002

(65) Prior Publication Data

US 2003/0054559 A1 Mar. 20, 2003

Related U.S. Application Data

(60) Provisional application No. 60/309,350, filed on Aug. 1, 2001.

(51) Int. Cl.[7] .......................... G01N 24/00; G01N 33/92
(52) U.S. Cl. ..................... 436/71; 436/173; 422/68.1; 324/307; 324/310; 324/311; 324/312
(58) Field of Search .......................... 422/68.1; 436/71, 436/173; 324/307, 310, 311, 312

(56) References Cited

U.S. PATENT DOCUMENTS

| 4,211,530 A | * | 7/1980 | Goverde et al. ............ 436/536 |
| 4,933,844 A | * | 6/1990 | Otvos ........................ 600/419 |
| 5,343,389 A | * | 8/1994 | Otvos ........................ 436/173 |

FOREIGN PATENT DOCUMENTS

JP          402116743 A    5/1990

OTHER PUBLICATIONS

Pharmar et al., "Detection of Vesicular Lipoproteins in Lecithin: cholsterol Acyltransferase–Deficient Plasma by 1H–NMR Spectroscopy," *Journal of Lipid Research*, 1989, vol. 30, No. 5, pp. 765–771.

* cited by examiner

Primary Examiner—Jan Ludlow
(74) Attorney, Agent, or Firm—Myers Bigel Sibley & Sajovec PA (57) ABSTRACT

A method of screening a subject for the presence of lipoprotein X includes the steps of: producing a measured lipid signal lineshape of an NMR spectrum of a blood plasma or serum sample obtained from a subject; generating a calculated lineshape for the sample, the calculated lineshape being based on derived concentrations of lipoprotein components potentially present in the sample, the derived concentration of each of the lipoprotein components being the function of a reference spectrum for that component and a calculated reference coefficient, wherein one of the lipoprotein components for which a concentration is calculated is lipoprotein X; and determining the degree of correlation between the calculated lineshape of the sample and the measured lineshape spectrum of the sample. This method can enable the practitioner, during a routine and easily-conducted cholesterol screening, to identify the presence of LP-X in a subject and begin diagnosis and treatment for conditions associated with LP-X (such as liver disease or LCAT deficiency).

15 Claims, 8 Drawing Sheets

METHOD OF DETERMINING PRESENCE AND CONCENTRATION OF LIPOPROTEIN X IN BLOOD PLASMA AND SERUM

RELATED APPLICATIONS

This application claims priority from U.S. Provisional Patent Application Ser. No. 60/309,350 filed Aug. 1, 2001, the contents of which are hereby incorporated by reference as if recited in full herein.

FIELD OF THE INVENTION

The present invention relates generally to the determination of constituents in blood plasma and serum and more specifically to the determination of lipoprotein constituents in blood plasma and serum.

BACKGROUND OF THE INVENTION

Lipoprotein X (LP-X) is an abnormal lipoprotein that appears in the sera of patients with obstructive jaundice. LP-X is a spherical particle typically between about 30 and 70 nm in diameter. Its density is between 1.006 and 1.063 g/ml, which is in the same range as normal low density lipoproteins (LDL). Phospholipids (about 66 percent) and unesterified cholesterol (about 22 percent) make up the bulk of LP-X; also, protein, cholesterol esters and triglycerides comprise about 12 percent of LP-X. See Narayanan, *Biochemistry and Clinical Relevance of Lipoprotein X*, 14 Annals of Clinical and Laboratory Science 371 (1984).

LP-X can be differentiated into three species: LP-X1; LP-X2; and LP-X3. Although these species vary slightly in the content of very low density lipoprotein, cholesterol and protein, they all have essentially the same phospholipid to free cholesterol ratio found in native LP-X.

Because LP-X can be indicative of obstructive jaundice, it can be a marker for cholestasis. In addition, LP-X is present in the plasma of patients with familial plasma lecithin: cholesterol acyl transferase (LCAT) deficiency; there is an inverse relationship between LP-X and LCAT activity.

LP-X is relatively rare, appearing in only about 0.1 percent of the population. Its presence can be very difficult to discern with standard cholesterol screening techniques; instead, it is typically identified through electrophoresis procedures, which are relatively laborious and provide results that are difficult to quantify. Nevertheless, identification of LP-X can be quite important in the treatment of a patient. For example, a patient whose lipid profile indicates an elevated cholesterol level (to which LP-X may contribute) may be treated for cardiovascular disease risk with a cholesterol-lowering "statin" drug while the presence of LP-X may indicate that the patient is actually suffering from liver disease or LCAT deficiency (not elevated LDL cholesterol), with the result that the aforementioned treatment may exacerbate, rather than address, the patient's condition. Therefore, it would be desirable to have a method of detecting LP-X that is relatively easily administered and accurate. It would also be desirable to have a method of detecting LP-X that would dovetail with routine tests being performed on a patient.

SUMMARY OF THE INVENTION

The present invention, as a first aspect, is directed to a method of screening a subject for the presence of lipoprotein X. The method comprises the initial step of producing a nuclear magnetic resonance (NMR) lipid signal lineshape of a blood plasma or serum sample obtained from a subject. Next, a calculated lineshape is generated for the sample, the lineshape being based on derived concentrations of lipoprotein components potentially present in the sample (the derived concentration of each of the lipoprotein components being the function of a reference spectrum for that component and a calculated reference coefficient), wherein one (or more) of the lipoprotein components for which a concentration is calculated is lipoprotein X. The method concludes with determining the degree of correlation between the calculated lineshape of the sample and the measured NMR lineshape of the sample. This method can enable the practitioner, during a routine and easily-conducted cholesterol screening, to identify the presence of LP-X in a subject and begin diagnosis and treatment of conditions associated with LP-X, or to prevent a subject from receiving medications for cholesterol management which may be deleterious.

In many instances, the method begins with a conventional NMR lipoprotein screening in which a calculated lineshape is generated based on derived concentrations of lipoprotein components in the sample, but in which no lipoprotein X component is included in the calculation. In such instances, a determination of the degree of correlation between the measured and calculated lineshapes will be below a predetermined number, thereby indicating the possible presence of a lipoprotein X constituent.

As a second aspect, the present invention is directed to a method of diagnosing a subject for the presence of lipoprotein X. The method comprises the steps of: acquiring an NMR spectrum of a blood plasma or serum sample obtained from the subject; and determining the presence of lipoprotein X in the sample based on the NMR spectrum of the sample. In certain embodiments, the inventive method can be conducted through the lineshape analysis described hereinabove.

As a third aspect, the present invention is directed to an apparatus for screening a subject for the presence of lipoprotein X. The apparatus comprises: an NMR spectromoeter for acquiring a lipid signal lineshape from an NMR spectrum of a blood plasma or serum sample; computer program means for storing the acquired lineshape of the sample; computer program means for storing reference spectra for each of a plurality of lipoprotein constituents, one (or more) of the constituents being lipoprotein X; computer program means for calculating a lineshape based on the concentrations of the lipoprotein constituents of the sample and the reference spectra; and computer program means for comparing the acquired lineshape and the calculated lineshape to determine whether there is sufficient correlation between the two. This apparatus can be employed to perform the methods set forth above and provide diagnosticians with an indication of LP-X presence during a routine cholesterol screening.

DETAILED DESCRIPTION OF EMBODIMENTS OF THE INVENTION

The present invention will now be described more fully hereinafter, in which embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. In the drawings, like numbers refer to like elements throughout, and thicknesses, size and dimensions of some components or features may be exaggerated for clarity. The order of operations and/or steps illustrated in the figures or recited in the claims are not intended to be limited to the order presented unless stated otherwise.

A. General Description of NMR Spectroscopy of Lipoproteins in Blood and Plasma $^1$H NMR spectra of human blood plasma contain two prominent peaks centered at approximately 1.2 and 0.8 ppm (relative to the chemical shift standard, TSP). These peaks arise from methylene ($CH_2$) and methyl ($CH_3$) protons, respectively, of plasma lipids. Each of these peaks is very heterogeneous in nature, consisting of overlapping resonances from protons of the several chemically distinct classes of lipids present in plasma: triglycerides; cholesterol; cholesterol esters; and phospholipids. These lipids are packaged together into three major classes of lipoprotein particles, which differ in the proportions of lipids which they contain. These lipoprotein particles also differ in density from which their names are derived: very low density lipoprotein (VLDL), low density lipoprotein (LDL), and high density lipoprotein (HDL).

These major classes of lipoprotein constituents may be further subdivided into subclasses. A subclass of lipoprotein particles comprises particles which have common physical properties, such as density, which permit a subclass to be fractionated from other subclasses and that exhibits NMR properties which are distinct from other subclasses. The NMR properties of one subclass may be distinct in a number of ways, such as chemical shift or lineshape variations, which make the subclass distinguishable from other subclasses. Subclasses distinguished upon density may be considered as a subclass of the class of lipoprotein which contains particles of the subclasses density. Delination of lipoprotein subclasses is discussed in U.S. Pat. No. 5,343,389 to Otvos, the disclosure of which is hereby incorporated herein in its entirety as if recited herein.

Only that fraction of the lipids in these lipoprotein particles that are in a fluid, mobile state (as opposed to an ordered liquid-crystalline state) contribute to the plasma lipid NMR resonances. The heterogeneity of these plasma signals is reflected by their complex lineshapes, which vary from person to person owing to variations of the plasma concentrations of the different lipoprotein particles, each of which has its own characteristically different NMR spectral properties.

NMR spectroscopy can be employed to determine the concentrations of lipoprotein classes (VLDL, LDL, HDL, and chylomicrons) and lipoprotein subclasses of a plasma sample, as well as a protein constituent, by a computer analysis of the lineshapes of its methyl and methylene signals (use of the methyl signal alone has been found to be preferable). This region of the observed plasma spectrum can be accurately represented by a simple linear combination of the spectra of the major lipoprotein and protein classes and/or subclasses noted above into which plasma can be fractionated by differential flotation ultracentrifugation.

The NMR spectral properties of these classes have been found to be quite similar from person to person. Thus, differences among the NMR signals form the plasma of individuals are caused by differences in the amplitudes of the lipid resonances for these constituents, which in turn are proportional to their concentrations in the plasma.

Figure 1:
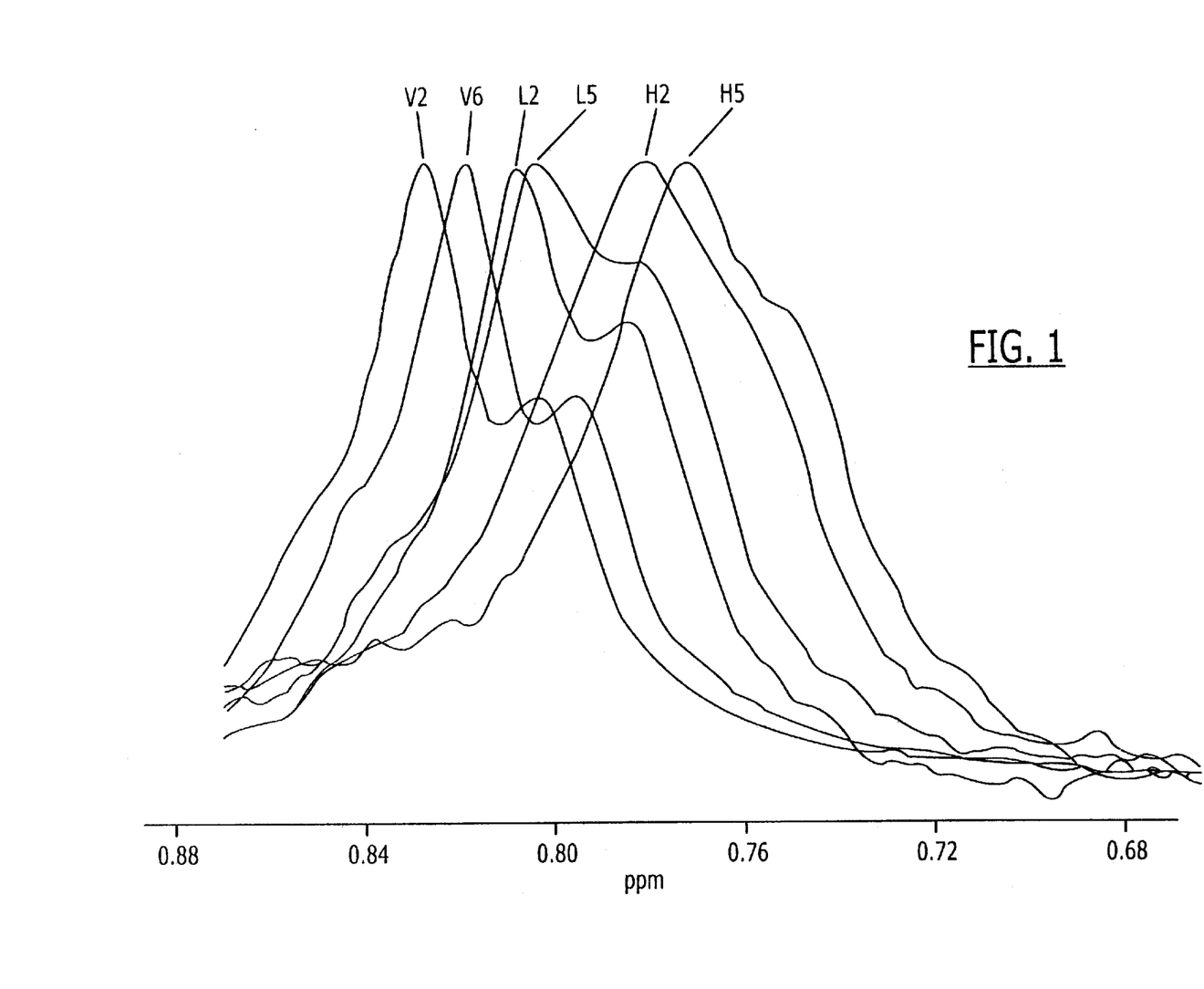
FIG. 1 is a graph showing the chemical shift spectra of a representative sample of lipoprotein constituent subclasses.
Figure 2:
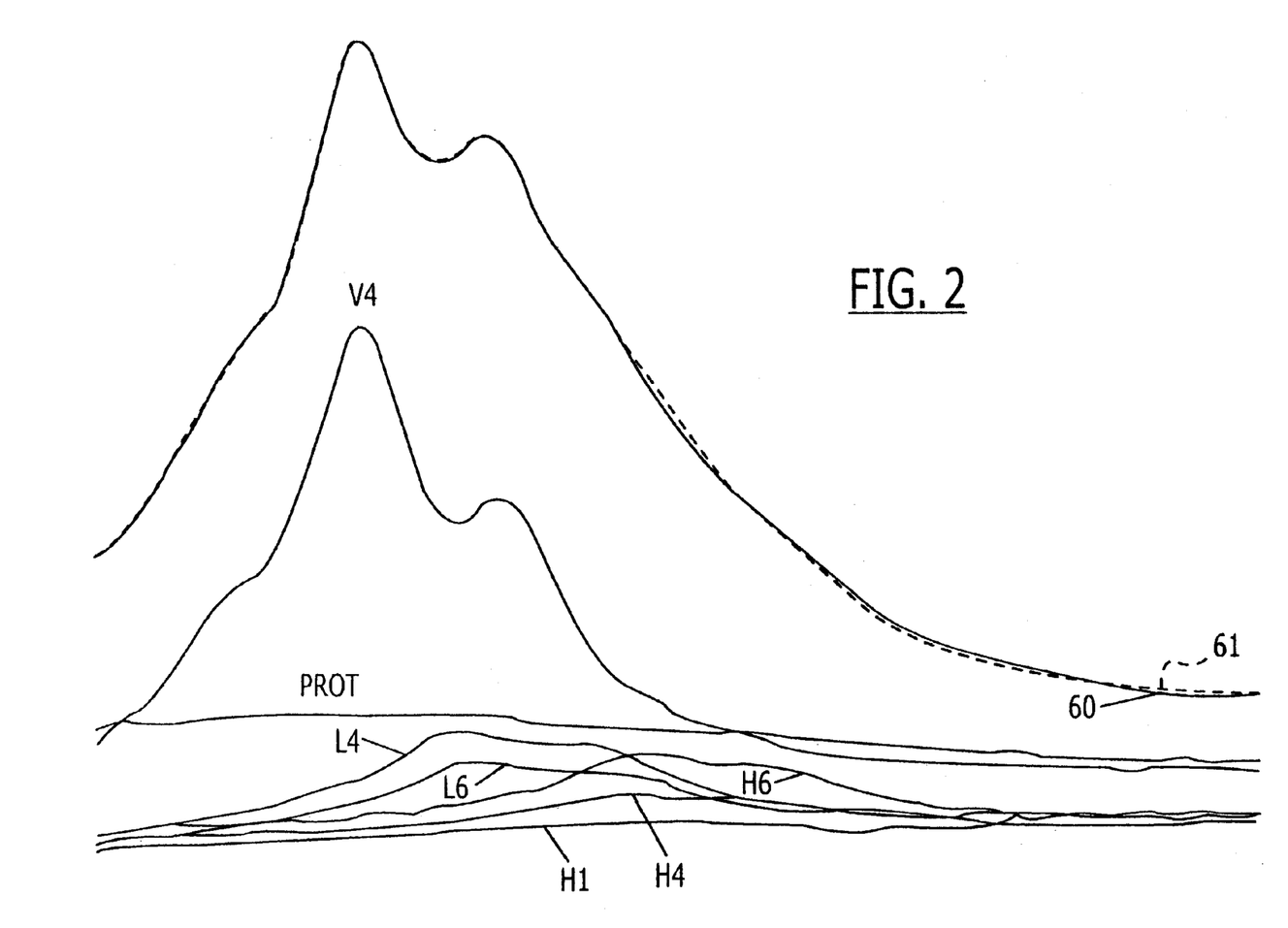
FIG. 2 is a graph illustrating NMR spectra for a plasma sample and the lipoprotein subclass and protein components thereof, with the peaks for methyl groups being illustrated.
Figure 3:
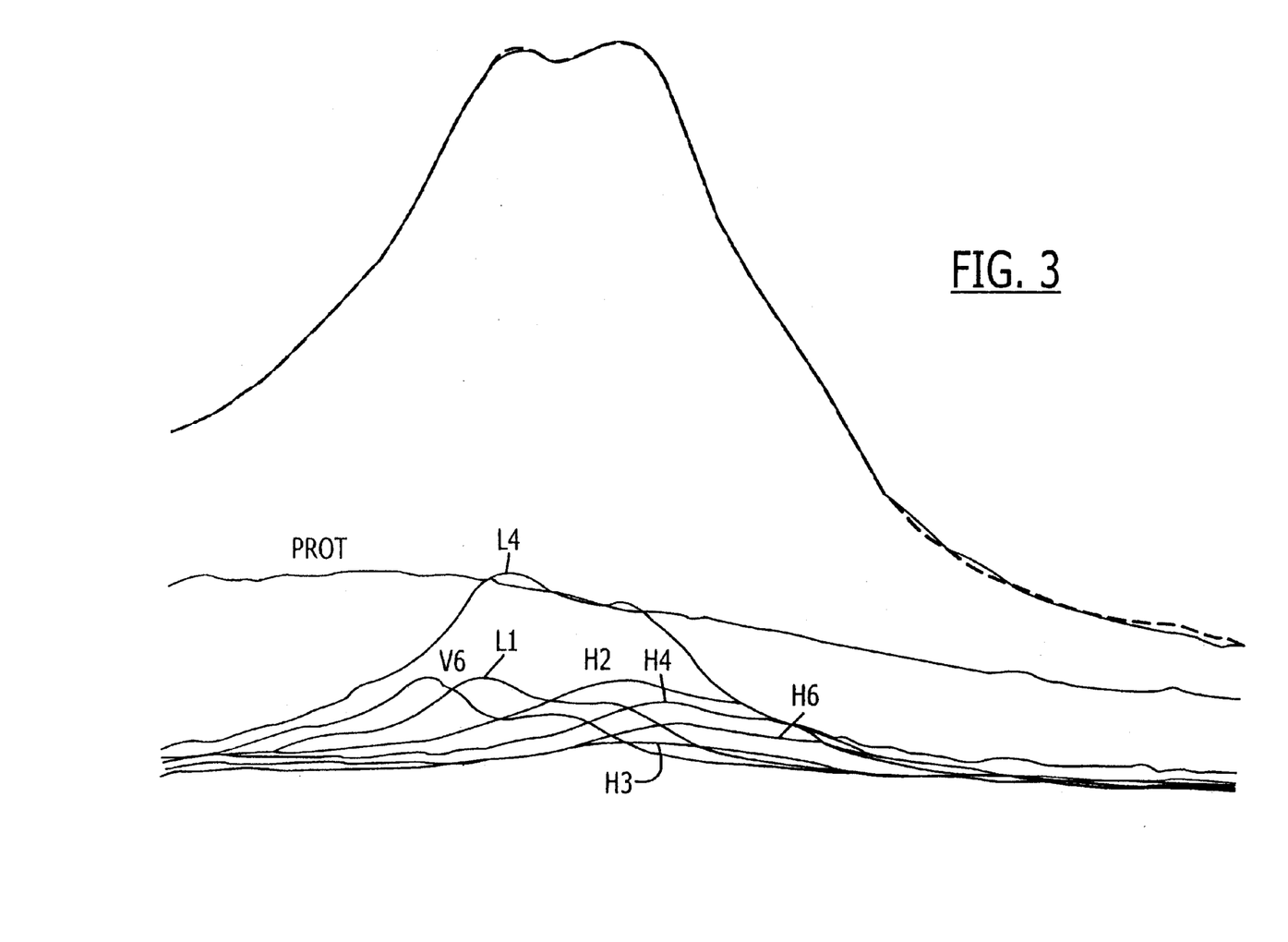
FIG. 3 is a graph illustrating NMR spectra for another plasma sample and the same lipoprotein subclass and protein components as shown in FIG. 2, with the peaks for methyl groups being illustrated.

The small person-to-person variations in the lineshapes of the lipoprotein classes are caused by the subclass heterogeneity known to exist within each of these lipoprotein classes. FIG. 1 shows the lineshapes and chemical shifts (positions) for a number of subclasses of lipoproteins. As shown in FIG. 1, the chemical shifts and lineshape differences between the subclasses are much smaller than those between the major lipoprotein classes, but are completely reproducible. Thus, differences among the NMR signals from the plasma of individuals are caused by differences in the amplitudes of the lipid resonances from the subclasses present in the plasma, which in turn are proportional to their concentrations in the plasma. This is illustrated in FIGS. 2 and 3 in which the NMR chemical shift spectra of two substantially different blood plasma samples are shown. The spectral peak produced by methyl ($CH_3$) protons 60 (shown as a solid line) is shown for the blood samples in FIGS. 2 and 3. The spectral peak 61 (shown as a dotted line) in FIGS. 2 and 3 is produced by the arithmetic sum of the NMR signals produced by the lipoprotein subclasses of the major classes VLDL, LDL, HDL, proteins and chylomicrons, as illustratively shown in FIG. 1. It can be seen that the lineshape of the whole plasma spectrum is dependent on the relative amounts of the lipoprotein subclasses whose amplitudes change dramatically with their relative concentrations in the plasma sample. It is the invariant lineshape of the NMR spectra of the subclasses of plasma lipoprotein constituents across the entire population and the fact that these lineshapes may be arithmetically added to produce the lineshape of the blood plasma sample, which is the basis for the present invention.

Since the observed $CH_3$ lineshapes of whole plasma samples are closely simulated by the appropriately weighted sum of lipid signals of its constituent lipoprotein classes, it is possible to extract the concentrations of these constituents present in any sample. This is accomplished by calculating the weighting factors which give the best fit between observed blood plasma NMR spectra and the calculated blood plasma spectra. Generally speaking, the process of NMR lipoprotein analysis can be carried out by the following steps: (1) acquisition of an NMR "reference" spectrum for each of the pure constituent lipoprotein classes and/or subclasses of plasma, (2) acquisition of a whole plasma NMR spectrum for a sample using measurement conditions identical to those used to obtain the reference spectra, and (3) computer deconvolution of the plasma NMR spectrum in terms of the constituent classes and/or subclasses to give the concentration of each lipoprotein constituent expressed as a multiple of the concentration of the corresponding lipoprotein reference. The plasma lineshape analysis is accomplished by calculating weighting coefficients for each of the reference NMR spectra which minimize the sum of squared deviations between the observed plasma NMR spectrum and that which is calculated by summing the weighted reference spectra. Typically, a correlation coefficient (calculated by the method described below) between the measured spectrum and the calculated lineshape of at least 0.999 indicates a successful deconvolution of the spectrum.

Although, as inferred above, the procedure can be carried out on lipoprotein classes, carrying out the process for subclasses of lipoproteins can decrease the error between the calculated lineshape and the NMR lineshape, thus increasing the accuracy of the measurement while allowing for simultaneous determination of the subclass profile of each class. Because the differences in subclass lineshapes and chemical shifts are small, it is typically important to correctly align the reference spectrum of each subclass with the plasma spectrum. The alignment of these spectra is accomplished by the alignment of control peaks in the spectra which are known to respond in the same manner to environmental variables, such as temperature and sample composition, as do the lipoprotein spectra. One such suitable alignment peak is the peak produced by CaEDTA, although other EDTA peaks may be utilized. By alignment of the spectra, the small variations in the subclasses' lineshapes and chemical shifts may be exploited to produce higher accuracy and subclass profiles.

Further description of these methods can be found in U.S. Pat. Nos. 4,933,844 and 5,343,389 to Otvos, the contents of which are hereby incorporated herein by reference in their entireties.

B. Mathematical Basis for Lineshape Comparison

The mathematics used in the lineshape fitting process (i.e., least squares fit of an unknown function in terms of a weighted sum of known functions) is well known and is described in many textbooks of numerical analysis, such as F. B. Hildebrand, Introduction to Numerical Analysis, 2nd edition, pp. 314–326, 539–567, McGraw-Hill, 1975.

To carry out the analysis, the data points of the real part of the sample plasma spectrum which comprise the spectral region to be fit (normally 0.73–0.85 ppm) are entered into an array. This plasma array consists of m discrete data points denoted $P_i^o$, i=1,2, ... m. The data points of the real part of the lipoprotein subspecies reference spectra for the same spectral region are entered into separate arrays. The data points of these arrays are denoted $V_{ji}$, where i=1,2, ... m data points and j=1,2, ... n constituents).

The method for fitting the measured sample plasma spectrum, $P_i^o$, with a linear combination of n constituent spectra is based on the premise that there are a set of coefficients (weighting factors), $c_j$, corresponding to the contributions of component j (lipoprotein subclass components and protein component), and a coefficient, $c_p^1$, corresponding to the imaginary portion of the sample plasma spectrum, such that for each data point, $P_i^o = P_i^c$, where $$P_i^c = \left(\sum_{j=1}^{n} c_j V_{ji}\right) + c_p^I V_i^I \quad \text{(calculated plasma spectrum)} \tag{1}$$

The best fit will be achieved when the root mean square error, $$\sqrt{\frac{1}{m-n}(\sum \epsilon_i^2)} \tag{2}$$

is minimized, where $\epsilon_1 = P_i^o - P_i^c$. This will be accomplished by finding those coefficients which minimize $\Sigma \epsilon_i^2$, that is, when $$\frac{\partial \Sigma \epsilon_i^2}{\partial c_j} = 0, \tag{3}$$

j=1,2, ... n+1 (n−1 subspecies components plus protein and plasma spectrum phase contributions). Differentiation results in n+1 simultaneous linear equations:

$$\sum_{i=1}^{m} P_i^o V_{ki} = \sum_{j=1}^{n+1} c_j \left(\sum_{j=1}^{M} V_{ki} V_{ji}\right), k = 1, 2, \ldots n+1 \tag{4}$$

If $$a_{kj} = \sum_{j=1}^{m} V_{ki} V_{ji} \text{ and } s_k = \sum_{i=1}^{m} P_i^o V_{ki} \tag{5}$$

then there are n+1 simultaneous linear equations of the form:

$$\sum_{j=1}^{m} c_j a_{kj} = s_k \quad k = 1, 2, \ldots n+1 \tag{6}$$

Forming the n+1×n+1 matrix, $[A]=[a_{kj}]$, j=1,2 ... n+1; k=1,2 ... n+1, gives [A]C=S, where C and S are the column vectors, $$\begin{bmatrix} c_1 \\ c_2 \\ \vdots \\ c_n \\ c_{n+1} \end{bmatrix} \text{ and } \begin{bmatrix} s_1 \\ s_2 \\ \vdots \\ s_n \\ s_{n+1} \end{bmatrix} \tag{7}$$

The coefficients providing the best fit are calculated by decomposition of the matrix [A] into a new set of in m×m matrices known collectively as the "singular value decomposition" of [A]:

$$[A]=[U][W][V]^T \tag{8}$$

where [U] is a matrix of orthogonal column vectors (scalar products=0), $[V]^T$ is the transpose of an orthogonal matrix [V], and [W] is a diagonal matrix with positive or zero elements, called "singular values:"

$$[W] = \begin{bmatrix} w_1 & 0 & \cdots & 0 \\ 0 & w_2 & \cdots & 0 \\ \vdots & \vdots & \ddots & \vdots \\ 0 & 0 & \cdots & w_m \end{bmatrix} \tag{9}$$

From this, $$[A]^{-1} = [V][W]^{-1}[U]^T \quad (10)$$

where $$[W]^{-1} = \begin{bmatrix} 1/w_1 & 0 & \cdots & 0 \\ 0 & 1/w_2 & \cdots & 0 \\ \vdots & \vdots & \ddots & \vdots \\ 0 & 0 & \cdots & 1/w_m \end{bmatrix} \quad (11)$$

which allows C to be solved for:

$$C = [V][W]^{-1}[U]^T S \quad (12)$$

where C is the best possible solution vector, provided that values of $w_j$ below a certain threshold value (selected by the user) are ignored ($1/w_j$ set to zero). These are the singular values which give rise to "ill-conditioned" linear combinations of near degenerate solutions, being most corrupted by roundoff errors. The actual solution of C is obtained by "back-substitution" in which $w_m$ is determined, allowing for the solution of $w_{m-1}$, etc.

The root mean square deviation (RMSD) is computed as $$\sigma_{RMS} = \sqrt{\frac{1}{m-n-1} \sum_{i=1}^{m} (P_i^o - P_i^c)^2} \quad (13)$$

The correlation coefficient is computed as $$r^p = \frac{\sum_{i=1}^{m} (P_i^o - \langle P_i^o \rangle)(P_i^c - \langle P_i^c \rangle)}{\sqrt{\left(\sum_{i=1}^{m} (P_i^o - \langle P_i^o \rangle)^2 \sum_{i=1}^{m} (P_i^c - \langle P_i^c \rangle)^2\right)}} \quad (14)$$

The component coefficients resulting from this lineshape analysis provide the concentrations of the lipoprotein and protein constituents in each plasma sample. Each concentration is expressed relative to the concentration of the lipoprotein whose spectrum is used as the reference. The final concentrations are normalized to the integrated area of the resonance from a trimethylacetate external standard sample run on the same day to correct for variations in the detection sensitivity of the NMR spectrometer.

In addition, the least squares method used for lipoprotein subclasses requires that the derived concentrations be positive. The latter constraint can be necessary when fitting plasma samples that may not contain one or more of the components included in the fit, because experimental errors in the data (noise) can cause the calculation to give negative concentrations for these components. When a negative coefficient is encountered it is constrained to zero, and the calculation is performed again, subject to that constraint.

Figure 4:
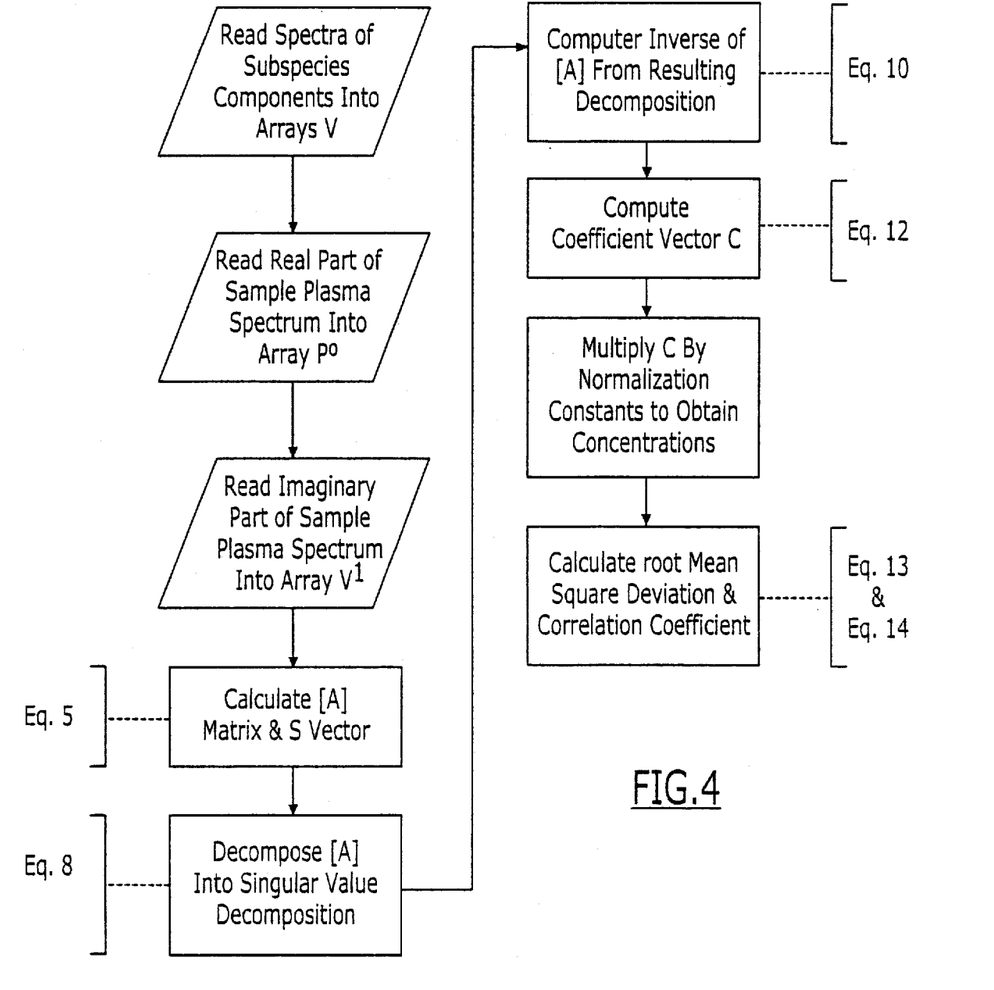
FIG. 4 is a flow chart illustrating a lineshape analysis for certain embodiments of the present invention.

FIG. 4 is a flow chart that demonstrates a general scheme for carrying out this analysis, with appropriate notation of equations.

C. Inaccuracies Introduced into NMR Spectroscopy by the Presence of Lipoprotein X in Sample As discussed above, LP-X is a low density lipoprotein of abnormal structure composed predominantly of phospholipids and unesterified cholesterol. Because its spectral properties are quite different from those of normal lipoproteins, its presence in a sample can significantly skew the NMR spectrum, and do so to the extent that the NMR method described above provides incorrect results.

Figure 5:
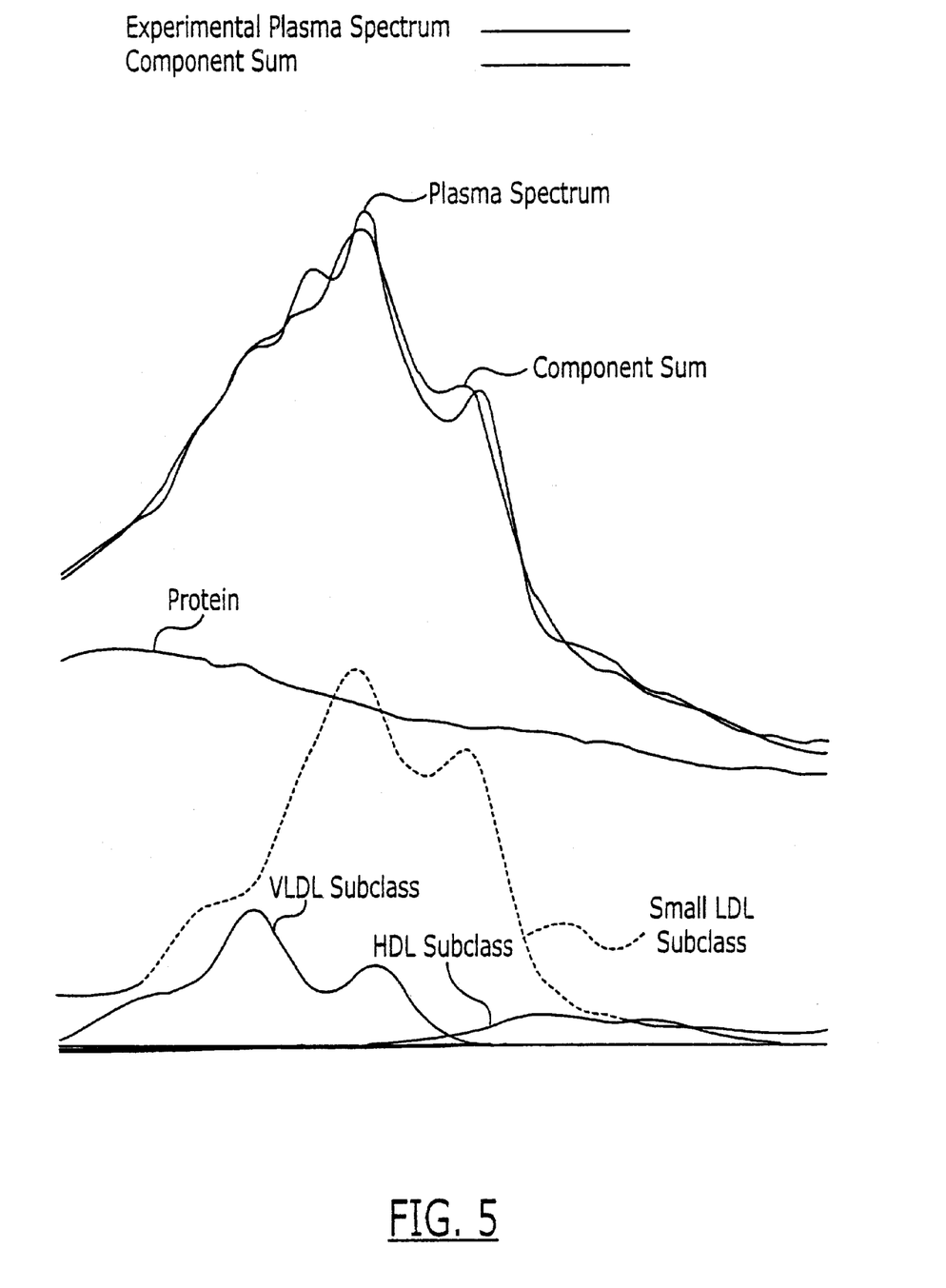
FIG. 5 is a graph illustrating NMR spectra for a plasma sample (methyl peaks) containing lipoprotein X generated by a prior art system that fails to consider the presence of lipoprotein X.

The inaccuracy caused by the presence of LP-X can be seen in FIG. 5. The darker line in FIG. 5 represents the measured lineshape of the methyl signal from a sample containing LP-X. The lighter line represents the calculated lineshape of the sample based on summation of the reference signals from fifteen normal lipoprotein subclasses. It is clear that the calculated lineshape does not accurately depict the measured spectrum. The correlation coefficient relating the calculated and measured lineshapes was 0.9972, which is considerably less than the desired value of >0.999. In this example, the calculation overemphasized the contribution of a small LDL subclass in trying to account for the signal from LP-X. As a result, the LDL cholesterol level was calculated to be much higher than it actually was. Standard chemical analysis of such a sample would also give an LDL cholesterol reading greatly in excess of the true amount of LDL present. It is possible, if not likely, that a diagnostician would interpret the inaccurate elevated LDL level as an indication of elevated cardiovascular disease risk. Such a condition would likely be treated aggressively with "statin" drug therapy, a treatment that would be ineffective for (or potentially even damaging to) a patient with the liver disease or LCAT deficiency typically associated with the presence of LP-X. Thus, not only would the condition associated with LP-X go untreated, but the treatment suggested by the incorrect LDL information might be deleterious to the subject.

D. Mathematical Basis for Calculation of Lineshape with LP-X Presence Considered In order to address the presence of LP-X in blood or plasma, Equation 1 set forth in Section B. above can be modified to include one or more additional components, $V_{ki}^x$ relating to LP-X, to give Equation 15 for the calculated plasma spectrum:

$$P_i^c = \left(\sum_{j=1}^{n} c_j V_{ji}\right) + \left(\sum_{k=1}^{l} c_k V_{ki}^x\right) + c_p^l V_i^l \quad (15)$$

Thus, a calculation originally performed with n $V_{ji}$ subclass components being summed without any consideration for LP-X would now be performed with 1 additional LP-X components (the flow chart of FIG. 4 is equally applicable here). In those samples that contain LP-X, the existence of LP-X can be discovered and its concentration accurately determined. With this information in hand, the diagnostician can focus on the conditions with which LP-X is associated.

E. Configuration of System for Acquiring and Calculating Lineshape

Figure 6:
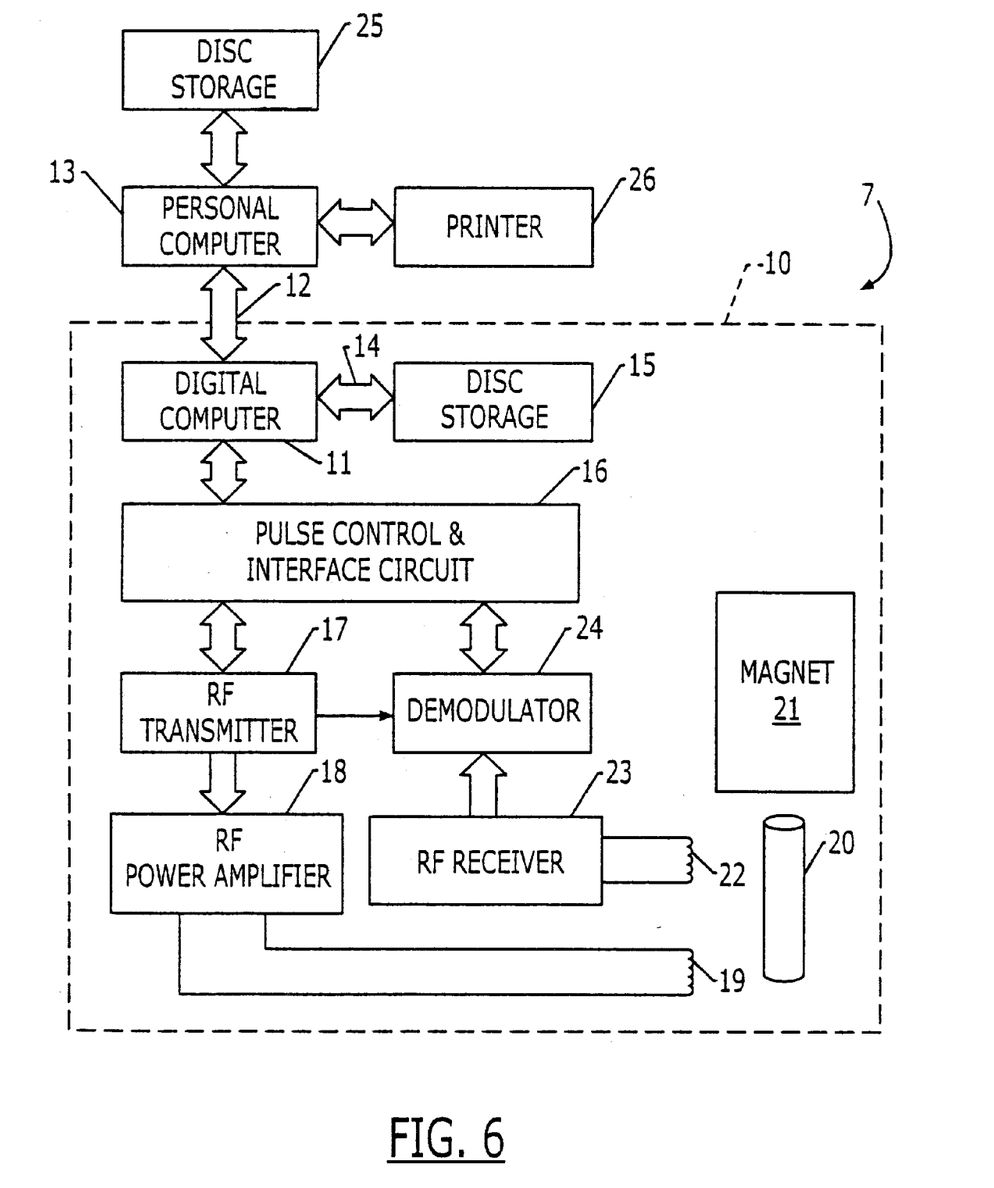
FIG. 6 is a block diagram of an apparatus of the present invention for measuring lipoprotein concentrations of a blood or plasma sample that is capable of detecting lipoprotein X.

Referring now to FIG. 6, a system 7 for acquiring and calculating the lineshape of a sample is illustrated therein. The system 7 includes an NMR spectrometer 10 for taking NMR measurements of a sample. In one embodiment, the spectrometer 10 is configured so that the NMR measurements are conducted at 400 MHz. Typically, a proton flow probe is installed, as is a temperature controller to maintain the sample temperature at 47+/−0.2 degrees C. Field homogeneity of the spectrometer 10 can be optimized by shimming on a sample of 99.8% $D_2O$ until the spectral linewidth of the HDO NMR signal is less than 0.6 Hz. The 90° RF excitation pulse width used for the $D_2O$ measurement is typically ca. 6–7 microseconds.

Referring again to FIG. 6, the spectrometer 10 is controlled by a digital computer 11 or other signal processing unit. The computer 11 should be particularly well suited for performing rapid Fourier transformations and may include for this purpose a hard-wired sine table and hardwired multiply and divide circuit. It may also include a data link 12 to an external personal computer 13, and a direct-memory-access channel 14 which connects to a hard disc unit 15.

The digital computer 11 may also include a set of analog-to-digital converters, digital-to-analog converters and slow device I/O ports which connect through a pulse control and interface circuit 16 to the operating elements of the spectrometer. These elements include an RF transmitter 17 which produces an RF excitation pulse of the duration, frequency and magnitude directed by the digital computer 11, and an RF power amplifier 18 which amplifies the pulse and couples it to the RF transmit coil 19 that surrounds sample cell 20. The NMR signal produced by the excited sample in the presence of a 9.4 Tesla polarizing magnetic field produced by superconducting magnet 21 is received by a coil 22 and applied to an RF receiver 23. The amplified and filtered NMR signal is demodulated at 24 and the resulting quadrature signals are applied to the interface circuit 16 where they are digitized and input through the digital computer 11 to a file in the disc storage 15.

After the NMR data are acquired from the sample in the measurement cell 20, processing by the computer 11 produces another file that is stored in the disc storage 15. This second file is a digital representation of the chemical shift spectrum and it is subsequently read out to the personal computer 13 for storage in its disc storage 25. Under the direction of a program stored in its memory, the personal computer 13 processes the chemical shift spectrum in accordance with the teachings of the present invention to print a report which is output to a printer 26. Those skilled in this art will recognize that other output devices, such as a computer display screen, may also be employed for the display of results.

It should be apparent to those skilled in the art that the functions performed by the personal computer 13 and its separate disc storage 25 may also be incorporated into the functions performed by the spectrometer's digital computer 11. In such case, the printer 26 may be connected directly to the digital computer 11. Other interfaces and output devices may also be employed, as is well-known to those skilled in this art.

F. Process for Acquiring and Calculating Lineshape

Reference samples of each lipoprotein and protein component to be analyzed are prepared (typically they are refrigerated during storage and allowed to warm prior to analysis) and placed within the spectrometer 10. An NMR measurement is then taken on each reference sample. The data for the reference samples is processed and stored in the computer 11. Techniques for acquiring and storing NMR spectroscopic data are well-known to those skilled in this art and need not be described in detail.

Referring now to FIG. 6, a system 7 for acquiring and calculating the lineshape of a sample is illustrated therein. The system 7 includes an NMR spectrometer 10 for taking NMR measurements of a sample. In one embodiment, the spectrometer 10 is configured so that the NMR measurements are conducted at 400 MHz. Typically, a proton flow probe is installed, as is a temperature controller to maintain the sample temperature at 47+/−0.2 degrees C. Field homogeneity of the spectrometer 10 can be optimized by shimming on a sample of 99.8% $D_2O$ until the spectral linewidth of the HDO NMR signal is less than 0.6 Hz. The 90° RF excitation pulse width used for the $D_2O$ measurement is typically ca. 6–7 microseconds.

Referring again to FIG. 6, the spectrometer 10 is controlled by a digital computer 11 or other signal processing unit. The computer 11 should be particularly well suited for performing rapid Fourier transformations and may include for this purpose a hard-wired sine table and hardwired multiply and divide circuit. It may also include a data link 12 to an external personal computer 13, and a direct-memory-access channel 14 which connects to a hard disc unit 15.

The digital computer 11 may also include a set of analog-to-digital converters, digital-to-analog converters and slow device I/O ports which connect through a pulse control and interface circuit 16 to the operating elements of the spectrometer. These elements include an RF transmitter 17 which produces an RF excitation pulse of the duration, frequency and magnitude directed by the digital computer 11, and an RF power amplifier 18 which amplifies the pulse and couples it to the RF transmit coil 19 that surrounds sample cell 20. The NMR signal produced by the excited sample in the presence of a 9.4 Tesla polarizing magnetic field produced by superconducting magnet 21 is received by a coil 22 and applied to an RF receiver 23. The amplified and filtered NMR signal is demodulated at 24 and the resulting quadrature signals are applied to the interface circuit 16 where they are digitized and input through the digital computer 11 to a file in the disc storage 15. The spectrometer can be configured to operate at other magnetic field strengths.

After the NMR data are acquired from the sample in the measurement cell 20, processing by the computer 11 produces another file that is stored in the disc storage 15. This second file is a digital representation of the chemical shift spectrum and it is subsequently read out to the personal computer 13 for storage in its disc storage 25. Under the direction of a program stored in its memory, the personal computer 13 processes the chemical shift spectrum in accordance with the teachings of the present invention to print a report which is output to a printer 26. Those skilled in this art will recognize that other output devices, such as a computer display screen, may also be employed for the display of results.

It should be apparent to those skilled in the art that the functions performed by the personal computer 13 and its separate disc storage 25 may also be incorporated into the functions performed by the spectrometer's digital computer 11 or other related computer equipment. In such case, the printer 26 may be connected directly to the digital computer 11. Other interfaces and output devices may also be employed, as is well-known to those skilled in this art.

As will be appreciated by one of skill in the art, the present invention may be embodied as an apparatus, a method, data or signal processing system, or computer program product. Accordingly, the present invention may take the form of an entirely software embodiment, or an embodiment combining software and hardware aspects. Furthermore, certain embodiments of the present invention may take the form of a computer program product on a computer-usable storage medium having computer-usable program code means embodied in the medium. Any suitable computer readable medium may be utilized including hard disks, CD-ROMs, optical storage devices, or magnetic storage devices.

The computer-usable or computer-readable medium may be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted or otherwise processed in a suitable manner if necessary, and then stored in a computer memory.

Computer program code for carrying out operations of the present invention may be written in an object oriented programming language such as Java®, Labview, Smalltalk or C++. However, the computer program code for carrying out operations of the present invention may also be written in conventional procedural programming languages, such as the "C" programming language or even assembly language. The program code may execute entirely on the user's (spectrometer) computer, partly on the user's computer as a stand-alone software package, partly on the user's computer and partly on a remote computer or entirely on the remote computer. In the latter scenario, the remote computer may be connected to the user's computer through wireless means and/or via a local area network (LAN) or a wide area network (WAN), or the connection may be made to an external computer (for example, through the Internet using an Internet Service Provider).

The flowcharts and block diagrams of certain of the figures herein illustrate the architecture, functionality, and operation of possible implementations of LP-X evaluation systems and/or programs according to the present invention. In this regard, each block in the flow charts or block diagrams represents a module, segment, operation, or portion of code, which comprises one or more executable instructions for implementing the specified logical function (s). It should also be noted that in some alternative implementations, the functions noted in the blocks may occur out of the order noted in the figures. For example, two blocks shown in succession may in fact be executed substantially concurrently or the blocks may sometimes be executed in the reverse order, depending upon the functionality involved.

Figure 7:
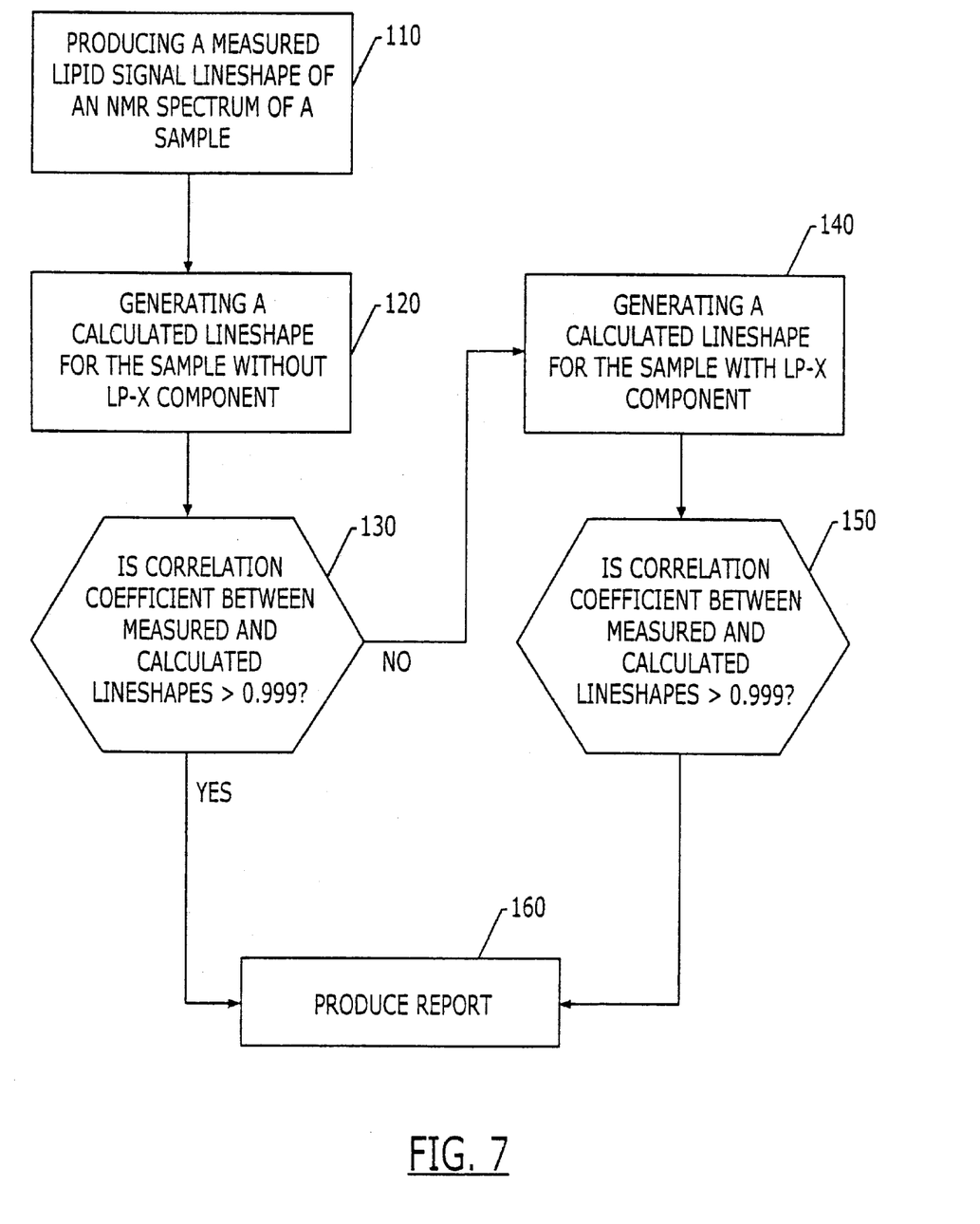
FIG. 7 is a flow chart illustrating certain embodiments of the method of the present invention.

FIG. 7 illustrates exemplary operations that may be carried out according to embodiments of the present invention. As shown, a measured lipid signal lineshape of an NMR spectrum of a sample can be produced (Block 110). Preferably, the preparation and acquisition of the measured sample is carried out under the same conditions as the reference samples. Typically, between about 8,000 and 16,000 NMR data points are acquired. A calculated lineshape for the sample without an LP-X component can be generated based on the derived concentrations of lipoprotein constituents present therein (Block 120). The correlation between the measured and calculated lineshapes can be evaluated (Block 130). For example, the coefficients of equation 1 above can be used to represent the concentrations of the constituents without the use of an LP-X component, and determining whether that calculated lineshape substantially matches the measured lineshape (e.g., whether the calculated lineshape has an acceptable predetermined correlation coefficient, such as about 0.999, with the measured lineshape (Decision Block 130)). If the correlation coefficient is not at an acceptable level, the lineshape analysis is repeated, such as by using equation 15 with the use of an additional term that represents LP-X (Block 140). The correlation coefficient is then recalculated and assessed to determine if the correlation between the measured and calculated lineshapes is acceptable (Block 150), again set at a suitable level such as greater than about 0.999. If the correlation is acceptable based on either (Decision Block 130 or 150), a report can be generated (Block 160). If based on the Decision Block 150, identification of the presence and/or concentration of LP-X can be noted.

The invention will now be described in more detail in the following non-limiting examples.

EXAMPLE 1

Acquisition of Reference Lineshape Data

A set of lipoprotein reference standards including chylomicrons, VLDL, LDL, and HDL subclasses of different size, and a "protein" fraction (density>1.21 g/ml) are prepared by fractionating plasma from normolipidemic and dyslipidemic subjects using a combination of preparative sequential ultracentrifugation and agarose gel filtration chromatography. A similar procedure is used to isolate LP-X and LP-X subclass reference standards, using plasma obtained from patients with obstructive liver disease containing very high concentrations of LP-X. Individual lipoprotein fractions are concentrated and dialyzed against a solution containing 0.12 M KCl, 5 mM EDTA, 1 mM $CaCl_2$, and 0.1% $NaN_3$, pH 7.4, and stored at 4° C. Prior to NMR measurement of these reference standards, the NMR spectrometer is shimmed using a 99.8% $D_2O$ sample to give a HDO signal linewidth at half height of <0.6 Hz. A sensitivity calibration is then performed using a standard sample containing 15 mM trimethylacetate, 5 mM EDTA, 3 mM $CaCl_2$, 0.12 M KCl in 10% $D_2O$. The integrated area of the trimethylacetate methyl signal is measured and recorded. Subsequently on a daily basis, the same measurement is performed under identical conditions prior to aquiring NMR spectra of plasma samples, with the ratio of the measured methyl signal area to that of the recorded area serving as the basis for normalizing the plasma NMR data to correct for day-to-day variations in the detection sensitivity of the NMR spectrometer.

Reference spectra of ca. 0.25 ml samples of the lipoprotein subclass standards introduced into the magnet in a flow mode via a Gilson 215 autosampler are then acquired at 47 degrees C. using a standard one-pulse sequence preceded by a 1.5 second selective decoupler presaturation pulse of the strong $H_2O$ resonance. A spatially selective composite 90° observation pulse ($90_x$–$90_y$–$90_{-x}$–$90_{-y}$) is used to minimize water suppression artifacts as described by A. Bax, "A Spatially Selective Composite 90° Radiofrequency Pulse", in J. Magn. Reson. 65, 142–145 (1985), although a normal 90° pulse can also give satisfactory results. The following acquisition parameters are used: 32 transients (4 dummy scans), 9K data size, 4500 Hz spectral width (10.0 to –1.25 ppm), 1.0 sec. acquisition time, 1.5 sec. decoupler presaturation pulse at the $H_2O$ frequency, 24 microsecond composite 90° pulse, and constant receiver gain for all spectra. The time-domain spectra (FIDs) of the lipoprotein reference samples are digitized and stored on computer disk.

The reference sample FIDs are processed identically to give the frequency-domain spectra used for the plasma lineshape fitting analysis. The processing operations of Fourier transformation, phasing, and baseline correction are accomplished using the standard commercial software of the NMR spectrometer (Bruker XWIN-NMR program). The FIDs are Fourier transformed using 32 K data points after application of a Gaussian window function. All spectra are scaled identically. The spectra are then phase corrected to give pure absorption mode signal.

EXAMPLE 2

Acquisition of Sample Lineshape Data

The procedure for acquiring plasma sample lineshape data is virtually the same as that described above for measurement of the reference samples. The same field-strength NMR spectrometer is used (400 MHz) and it is set up to operate in the identical fashion used to acquire the lipoprotein reference spectra. The time domain spectrum (FID) of the plasma sample is acquired in the identical fashion as the reference spectra, except that duplicate 8-transient spectra are acquired rather than a single 32-transient spectrum. Processing is carried out in an identical manner to produce a digitized representation of the blood plasma sample spectrum in the disk of the personal computer. The whole plasma spectrum is then accurately referenced to the sharp NMR resonance peak produced by the calcium complex of EDTA which is present in the sample. The sample spectrum and the reference spectra are shifted as needed to align the CaEDTA peak at 2.519 ppm on the horizontal scale.

The mathematics used in the lineshape fitting process (i.e., non-negative linear least squares fit of an unknown function in terms of a weighted sum of known functions) is well known and is described in many textbooks of numerical analysis and in articles such as D. J. Leggett, *Numerical Analysis of Multicomponent Spectra,* Analytical Chemistry 49, 276–281 (1977). A program for performing this function on a PC-AT computer is described in U.S. Pat. No. 5,343,389 to Otvos.

EXAMPLE 3

Results of Lineshape Analysis with LP-X Calculations

Figure 8:
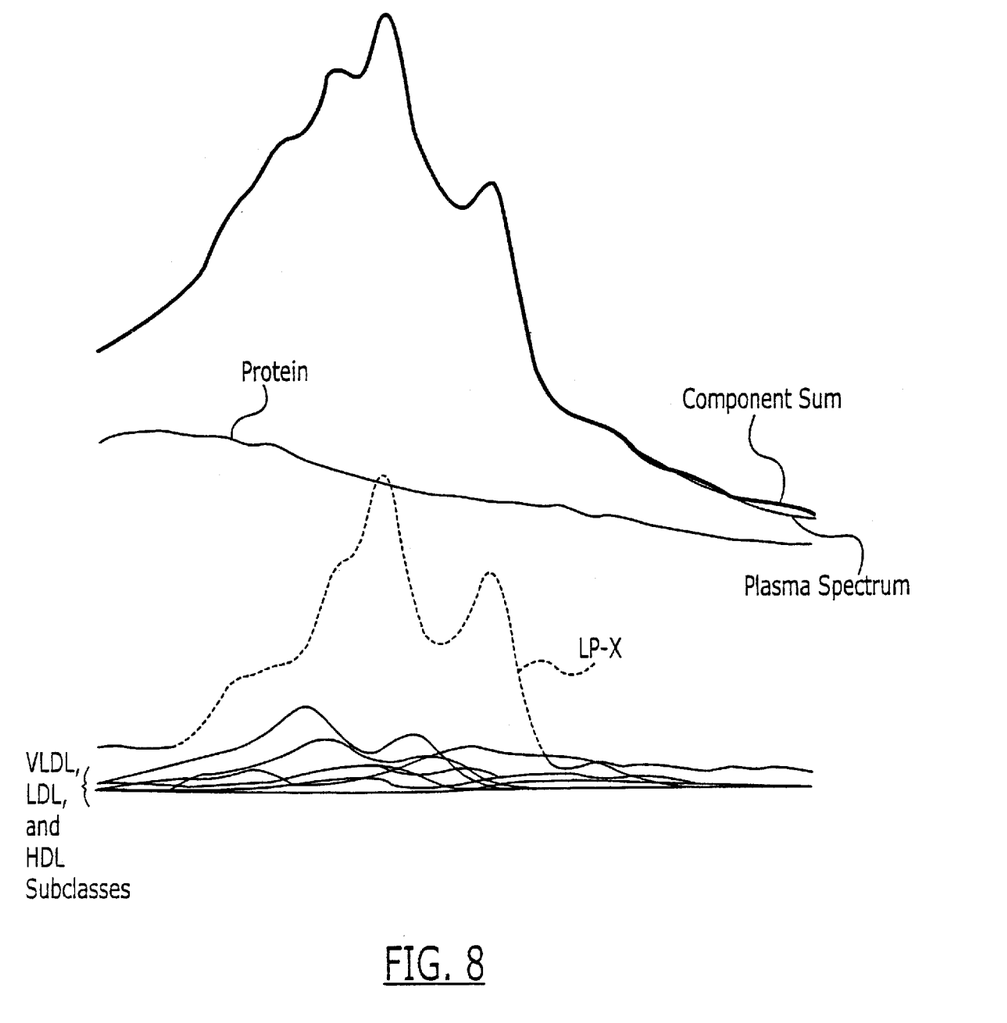
FIG. 8 is a graph illustrating NMR spectra (methyl peaks) for the same plasma sample as used in FIG. 5 generated by a system of the present invention that considers the presence of lipoprotein X.

The results of the procedure outlined in Examples 1 and 2 can be seen in FIG. 8. The sample analyzed therein (which was the same sample as was analyzed in FIG. 5) clearly contains a high concentration of LP-X. As can be seen in FIG. 8, the calculated lineshape gives a much closer fit to that of the measured lineshape of the sample than is the case for the calculated lineshape of FIG. 5 due to the altered calculation technique described above, which includes reference spectra for LP-X in the analysis model.

These results also enable a practitioner to identify this sample as one having LP-X. Consequently, the practitioner can proceed with identifying and treating the condition (such as cholestasis or LCAT deficiency) associated with LP-X.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method of screening a subject for the presence of lipoprotein X, comprising the steps of:
   (a) producing a measured lipid signal lineshape from an NMR spectrum of a blood plasma or serum sample obtained from a subject;
   (b) generating a calculated lineshape for the sample, the calculated lineshape being calculated based on derived concentrations of lipoprotein components potentially present in the sample, the derived concentration of each of the lipoprotein components being the function of a reference spectrum for that component and a calculated reference coefficient, wherein one of the lipoprotein components for which a concentration is calculated is lipoprotein X; and
   (c) determining the degree of correlation between the calculated lineshape and the measured lineshape of the sample.

2. The method defined in claim 1, further comprising the steps of:
   (d) generating an initial calculated lineshape for the sample, the initial calculated lineshape being calculated based on derived concentrations of lipoprotein components potentially present in the sample, the derived concentration of each of the lipoprotein components being the function of a reference spectrum for that component and a calculated reference coefficient, wherein none of the lipoprotein components for which a concentration is calculated is lipoprotein X; and
   (e) determining that the degree of correlation between the initial calculated lineshape and the measured lineshape of the sample is below a predetermined number;
   wherein steps (d) and (e) are carried out after step (a).

3. The method defined in claim 1, wherein the generating step comprises calculating the reference coefficients for the calculated lineshape based on a linear least squares fit technique.

4. The method defined in claim 1, wherein the reference spectra for the plurality of lipoprotein constituents includes spectra for lipoprotein subclasses.

5. The method defined in claim 1, further comprising the step of producing a report listing the concentrations of the lipoprotein constituents present in the sample.

6. A method of diagnosing a subject for the presence of lipoprotein X, comprising the steps of:
   acquiring an NMR spectrum of a blood plasma or serum sample obtained from the subject; and
   determining the presence of lipoprotein X in the sample based on the NMR spectrum of the sample.

7. The method defined in claim 6, wherein the acquiring step comprises:
   (a) producing a measured lipid signal lineshape for an NMR spectrum of a blood plasma or serum sample obtained from a subject;
   (b) generating an initial calculated lineshape for the sample, the initial calculated lineshape being based on derived concentrations of lipoprotein components potentially present in the sample, the derived concentration of each of the lipoprotein components being the function of a reference spectrum for that component and a calculated reference coefficient, wherein none of the lipoprotein components for which a concentration is calculated is lipoprotein X;
   (c) determining that the degree of correlation between the initial calculated lineshape of the sample and the measured lineshape of the sample is below a predetermined number; and (d) generating a subsequent calculated lineshape for the sample, the subsequent calculated lineshape being based on derived concentrations of lipoprotein components potentially present in the sample, the derived concentration of each of the lipoprotein components being the function of a reference spectrum for that component and a calculated reference coefficient, wherein one of the lipoprotein components for which a concentration is calculated is lipoprotein X.

8. The method defined in claim 7, wherein steps (b) and (d) comprise calculating the reference coefficients for the initial and subsequent calculated lineshapes based on a linear least squares fit technique.

9. The method defined in claim 7, wherein the reference spectra for the plurality of lipoprotein constituents includes spectra for lipoprotein subclasses.

10. The method defined in claim 6, further comprising the step of producing a report listing the concentrations of the lipoprotein constituents present in the sample.

11. The method defined in claim 6, further comprising the step of identifying one of liver disease and LCAT deficiency in the subject following the determining step.

12. An apparatus for screening a subject for the presence of lipoprotein X, comprising:

an NMR spectrometer for acquiring a measured lipid signal lineshape of an NMR spectrum of a blood plasma or serum sample;

computer program means for storing the measured lineshape of the sample;

computer program means for storing reference spectra for each of a plurality of lipoprotein constituents, one of the constituents being lipoprotein X;

computer program means for calculating a calculated lineshape based on the derived concentrations of the lipoprotein constituents of the sample and the reference spectra;

computer program means for comparing the lipid signal lineshape and the calculated lineshape to determine whether the calculated lineshape substantially matches the measured lineshape.

13. The apparatus defined in claim 12, wherein the computer program means for storing reference spectra comprise means for storing lipoprotein subclass spectra.

14. The apparatus defined in claim 12, further comprising an output device for producing a report indicating the presence of lipoprotein X.

15. The apparatus defined in claim 12, further comprising means for signaling an analyst when the calculated lineshape does not substantially match the measured lineshape within a predetermined correlation coefficient.

* * * * *